US009826938B2

United States Patent
Liu et al.

(10) Patent No.: US 9,826,938 B2
(45) Date of Patent: Nov. 28, 2017

(54) MOTION COMPENSATION FOR OPTICAL HEART RATE SENSORS

(71) Applicant: Microsoft Technology Licensing, LLC, Redmond, WA (US)

(72) Inventors: Zongyi Liu, Issaquah, WA (US); Christopher Lance Nuesmeyer, Renton, WA (US); Haithem Albadawi, Redmond, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 106 days.

(21) Appl. No.: 14/853,827

(22) Filed: Sep. 14, 2015

(65) Prior Publication Data

US 2016/0120476 A1 May 5, 2016

Related U.S. Application Data

(60) Provisional application No. 62/072,362, filed on Oct. 29, 2014.

(51) Int. Cl.
*A61B 5/02* (2006.01)
*A61B 5/00* (2006.01)
(Continued)

(52) U.S. Cl.
CPC .......... *A61B 5/721* (2013.01); *A61B 5/02427* (2013.01); *A61B 5/01* (2013.01); *A61B 5/681* (2013.01); *A61B 2562/0219* (2013.01)

(58) Field of Classification Search
CPC . A61B 5/721; A61B 5/02427; A61B 5/02438; A61B 5/024; A61B 5/02416
See application file for complete search history.

(56) References Cited

U.S. PATENT DOCUMENTS 6,810,277 B2   10/2004   Edgar et al.
6,905,470 B2   6/2005    Lee et al.
(Continued)

FOREIGN PATENT DOCUMENTS

JP      2003310562 A    11/2003
KR      20050017254 A   2/2005
(Continued)

OTHER PUBLICATIONS

Fingas, J., "TomTom's New GPS Watches Track Your Heart Rate Without a Chest Strap," Engadget Website, Available Online at http://www.engadget.com/2014/04/03/tomtom-cardio-gps-watches/, Apr. 3, 2014, 8 pages.
Goode, L., "Samsung's New Gear Fit Needs to Work on the 'Fit' Part," re/code Website, Available Online at http://recode.net/2014/04/08/samsungs-new-gear-fit-needs-to-work-on-the-fit-part/, Apr. 8, 2014, 9 pages.
(Continued)

*Primary Examiner* — Robert N Wieland
(74) *Attorney, Agent, or Firm* — Alleman Hall Creasman & Tuttle LLP

(57) ABSTRACT

A method of optical heart rate sensing includes receiving a motion frequency from a motion sensor and receiving an optical signal from an optical sensor. The motion frequency is then filtered from the optical signal, and an estimated heart rate frequency is determined based on the filtered optical signal. A heart rate is reported that is based on the motion frequency, but not based on the estimated heart rate frequency, when a local neighbor magnitude ratio of the estimated heart rate frequency is below a confidence threshold.

18 Claims, 8 Drawing Sheets

(51) Int. Cl.
*A61B 5/024* (2006.01)
*A61B 5/01* (2006.01)

(56) References Cited

U.S. PATENT DOCUMENTS

| | | | |
|---|---|---|---|
| 7,018,338 | B2 | 3/2006 | Vetter et al. |
| 7,993,276 | B2 | 8/2011 | Nazarian et al. |
| 8,655,436 | B2 | 2/2014 | Shimizu et al. |
| 2006/0084879 | A1* | 4/2006 | Nazarian ............ A61B 5/02438 600/500 |
| 2009/0281435 | A1 | 11/2009 | Ahmed et al. |
| 2010/0113948 | A1 | 5/2010 | Yang et al. |
| 2011/0098583 | A1 | 4/2011 | Pandia et al. |
| 2014/0058217 | A1 | 2/2014 | Giovangrandi |

FOREIGN PATENT DOCUMENTS

| | | |
|---|---|---|
| WO | 2009071128 A1 | 6/2009 |
| WO | 2013038296 A1 | 3/2013 |

OTHER PUBLICATIONS

NDTV Correspondent, "Samsung Gear Fit, Gear 2 and Gear 2 Neo Go on Sale Worldwide," NDTV Gadgets360 Website, Available Online at http://gadgets.ndtv.com/wearables/news/samsung-gear-fit-gear-2-and-gear-2-neo-go-on-sale-worldwide-507220, Apr. 11, 2014, 3 pages.

Poeter, D., "Meet Simband, Samsung's Next-Gen Health Tracker," PC Mag Website, Available Online at http://www.pcmag.com/article2/0,2817,2458663,00.asp, May 28, 2014, 18 pages.

Pandia, et al., "Motion Artifact Cancellation to Obtain Heart Sounds from a Single Chest-Worn Accelerometer" In IEEE International Conference on Acoustics Speech and Signal Processing, Mar. 14, 2010, 4 pages.

Wang, et al., "Multichannel Reflective PPG Earpiece Sensor with Passive Motion Cancellation", In IEEE Transactions on Biomedical Circuits and Systems, Dec. 2007, 7 pages.

Han, et al., "Development of a Wearable Health Monitoring Device with Motion Artifact Reduced Algorithm", In International Conference on Control, Automation and Systems, Oct. 17, 2007, 4 pages.

* cited by examiner

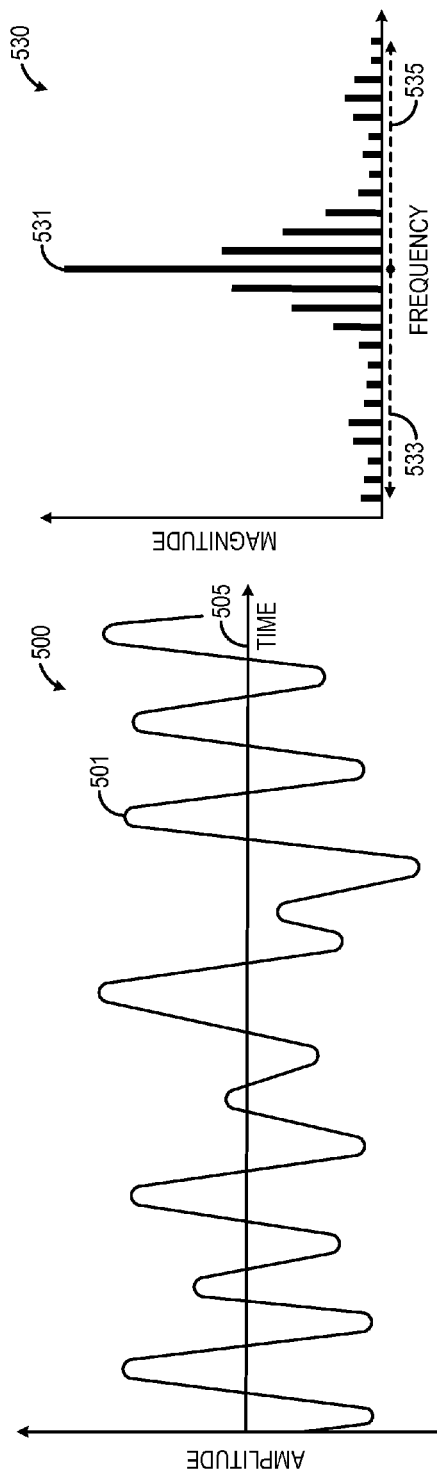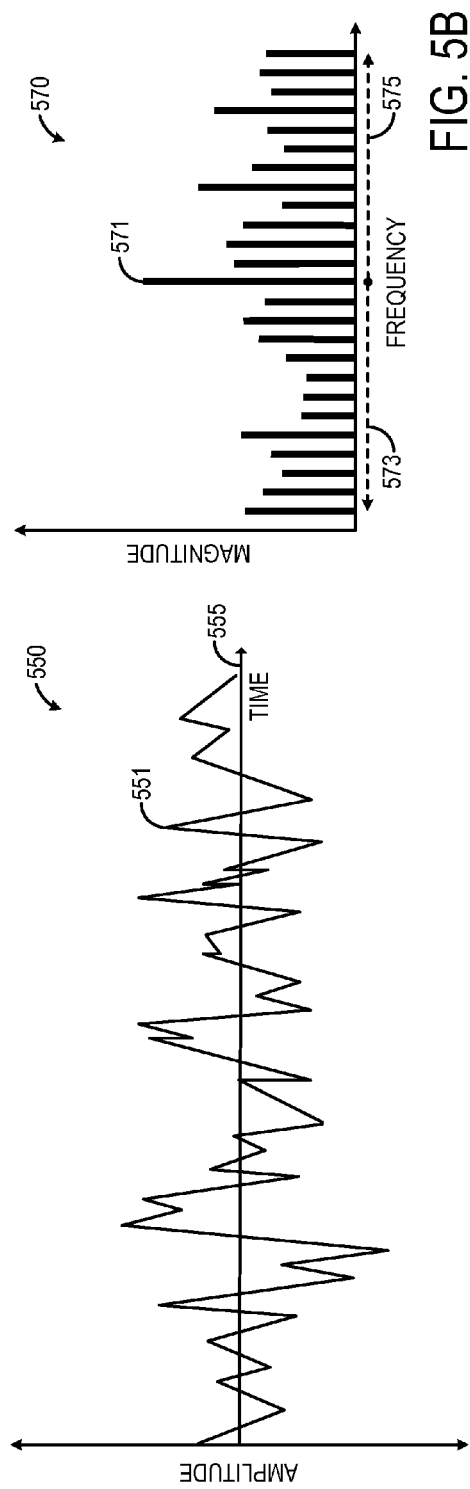

MOTION COMPENSATION FOR OPTICAL HEART RATE SENSORS

CROSS REFERENCE TO RELATED APPLICATIONS

This application claims priority to U.S. Provisional Patent Application No. 62/072,362, filed Oct. 29, 2014, and titled "MOTION COMPENSATION FOR OPTICAL HEART RATE SENSORS", the entire disclosure of which is incorporated by reference for all purposes.

BACKGROUND

Monitoring heart rate levels provides useful health information. Optical heart rate sensors provide a non-invasive means of determining heart rate levels. An optical heart rate sensor may be incorporated into a wearable device.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

A method of optical heart rate sensing includes receiving a motion frequency from a motion sensor and receiving an optical signal from an optical sensor. The motion frequency is then filtered from the optical signal, and an estimated heart rate frequency is determined based on the filtered optical signal. A heart rate is reported that is based on the motion frequency, but not based on the estimated heart rate frequency, when a local neighbor magnitude ratio of the estimated heart rate frequency is below a confidence threshold.

BRIEF DESCRIPTION OF THE DRAWINGS

FIGS. 5A & 5B show example filtered optical signals in both the time domain and the frequency domain.

DETAILED DESCRIPTION

Figures 1A, 1B:
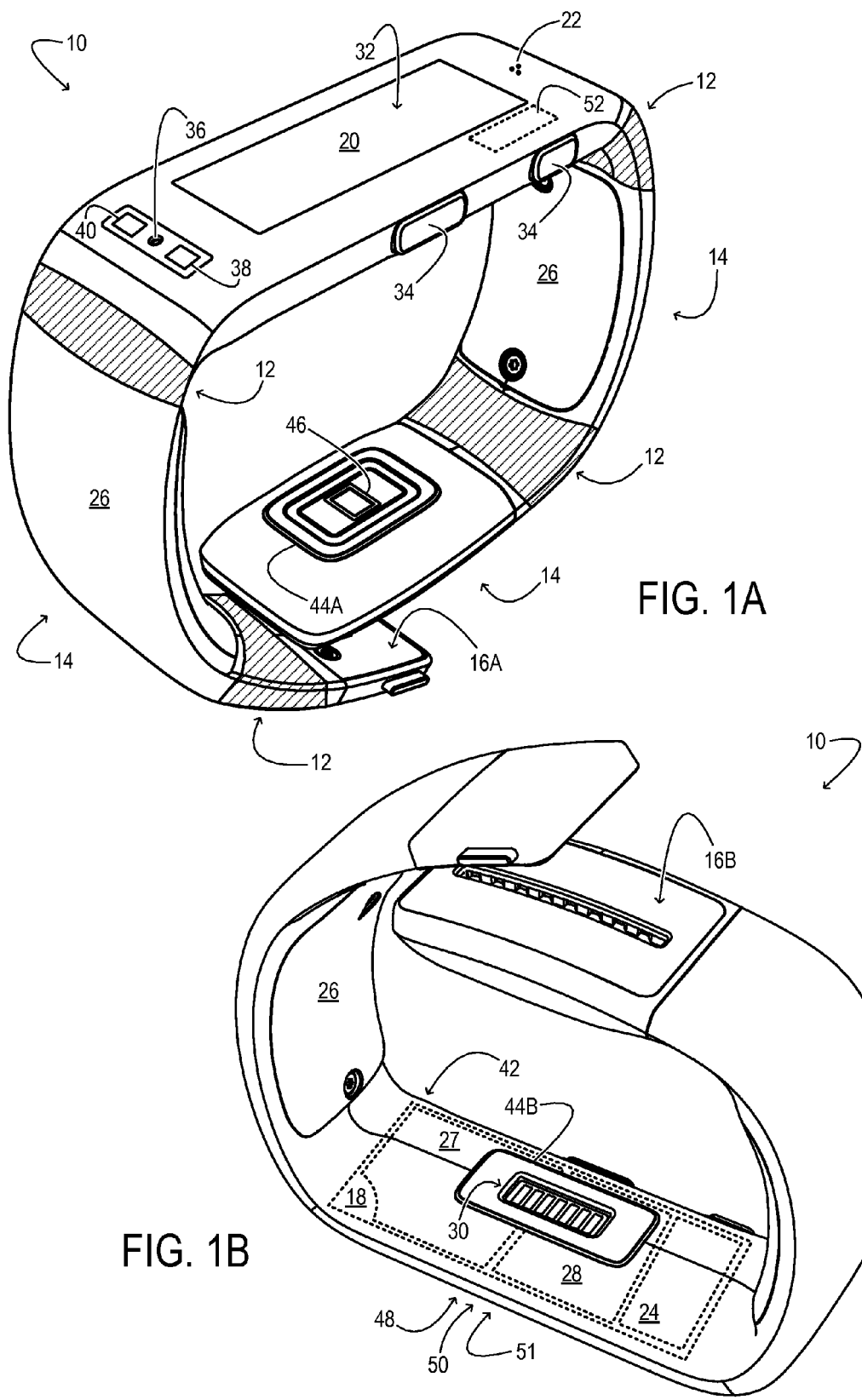
FIGS. 1A and 1B show a wearable electronic device.

The present disclosure is directed to motion compensation for an optical heart rate sensor. While described below in the context of a wearable computing device, it is to be understood that applying motion compensation to an optical signal for an optical heart rate sensor, as described herein, may be used in numerous different applications, and with various different types of sensory-and-logic systems.

Incorporating an optical heart rate sensor into a wearable computing device allows a user to monitor health factors, such as heart rate, calories burned, response to exertion exercises, heart rate variability, etc. However, the signal from the optical sensor may degrade in quality with increased motion, as user motion may change the optical properties of the skin, tissues, blood vessels, and/or liquid blood beneath the optical sensor. As such, motion compensation may be applied to an optical signal as part of discerning a heart rate from the optical signal. A motion frequency may be determined based on other sensor inputs, such as accelerometers, gyroscopes, or optical signals from different wavelength spectrums. The motion frequency may then be suppressed from the signals received from the optical heart rate sensor.

However, motion compensation presents additional challenges during scenarios where the motion frequency is similar to the heart rate frequency, and/or where harmonic frequencies of the motion frequency are similar to the heart rate frequency, as the motion compensation may also remove the heart rate signal, leaving only random noise in the compensated optical signal.

Motion compensation algorithms may utilize an adaptive approach, where the amount of motion compensation decreases when the motion frequency approaches the heart rate frequency. However, such adaptive algorithms may result in inaccurate heart rates being reported in certain scenarios. Decreasing the amount of motion compensation will result in a noisier optical signal, which may yield an inaccurate estimation of heart rate. If there is a lag in the heart rate tracking algorithm, aggressive motion compensation may still be applied while the motion frequency is similar to the heart rate frequency, thereby suppressing the heart rate before the level of motion compensation is reduced. Further, if a decreased amount of motion compensation is applied when the heart rate frequency is no longer similar to the motion frequency, the compensated optical signal will still contain motion artifacts.

According to this disclosure, motion frequency is filtered from an optical heart rate signal, and an estimated heart rate frequency is determined based on the filtered optical signal. A local neighbor magnitude ratio is then determined for the estimated heart rate frequency, which indicates a probability that the estimated heart rate frequency represents the actual heart rate frequency as compared to neighboring frequencies. If the local neighbor magnitude ratio is above a confidence threshold, heart rate is reported based on the estimated heart rate frequency. The motion frequency may be used as a proxy for heart rate frequency when the local neighbor magnitude ratio for the estimated heart rate frequency is below the confidence threshold. In this way, an accurate heart rate may be reported while applying a constant amount of motion compensation to the optical signal.

FIGS. 1A and 1B show aspects of an example sensory-and-logic system in the form of a wearable electronic device 10. The illustrated device is band-shaped and may be worn around a wearer's wrist. Wearable electronic device 10 includes at least four flexion regions 12 linking less flexible regions 14. The flexion regions 12 of wearable electronic device 10 may be elastomeric in some examples. Fastening componentry 16A and 16B is arranged at both ends of wearable electronic device 10. The flexion regions 12 and fastening componentry 16A and 16B enable wearable electronic device 10 to be closed into a loop and to be worn on a wearer's wrist. In other implementations, a sensory-and-logic system may be implemented in the form of wearable electronic devices having a more elongate band shape which may be worn around a wearer's bicep, waist, chest, ankle, leg, head, or other body part. Such a wearable electronic device, for example, may take the form of eye glasses, a head band, an arm-band, an ankle band, a chest strap, or an implantable device to be implanted in tissue.

Wearable electronic device 10 includes various functional components integrated into flexible regions 14. In particular, wearable electronic device 10 includes a compute system 18, display 20, loudspeaker 22, communication suite 24, and various sensors. These components draw power from one or more energy-storage cells 26. A battery—e.g., a lithium ion battery—is one type of energy-storage cell suitable for this purpose. Examples of alternative energy-storage cells include super- and ultra-capacitors. In examples where wearable electronic device 10 is configured to be worn on a wearer's wrist, energy-storage cells 26 may be curved to fit the wrist, as shown in the drawings.

In general, energy-storage cells 26 may be replaceable and/or rechargeable. In some examples, recharge power may be provided through a universal serial bus (USB) port 30, which includes a magnetic latch to releasably secure a complementary USB connector. In other examples, energy-storage cells 26 may be recharged by wireless inductive or ambient-light charging. In still other examples, wearable electronic device 10 may include electro-mechanical componentry to recharge the energy storage cells from the user's adventitious or purposeful body motion. For example, batteries or capacitors may be charged via an electromechanical generator integrated into wearable electronic device 10. The generator may be turned by a mechanical armature that turns while the wearer is moving and wearing wearable electronic device 10.

In wearable electronic device 10, compute system 18 is situated below display 20 and operatively coupled to display 20, along with loudspeaker 22, communication suite 24, and the various sensors. Compute system 18 includes a data-storage machine 27 to hold data and instructions, and a logic machine 28 to execute the instructions. Aspects of compute system 18 are described in further detail with reference to FIG. 7.

Display 20 may be any suitable type of display. In some configurations, a thin, low-power light emitting diode (LED) array or a liquid-crystal display (LCD) array may be used. An LCD array may be backlit in some implementations. In other implementations, a reflective LCD array (e.g., a liquid crystal on silicon, LCOS array) may be frontlit via ambient light. A curved display may also be used. Further, active matrix organic LED (AMOLED) displays or quantum dot displays may be used.

Communication suite 24 may include any appropriate wired or wireless communications componentry. In FIGS. 1A and 1B, communication suite 24 includes USB port 30, which may be used for exchanging data between wearable electronic device 10 and other computer systems, as well as providing recharge power. Communication suite 24 may further include two-way Bluetooth, Wi-Fi, cellular, near-field communication and/or other radios. In some implementations, communication suite 24 may include an additional transceiver for optical, line-of-sight (e.g., infrared) communication.

In wearable electronic device 10, touch-screen sensor 32 is coupled to display 20 and configured to receive touch input from the wearer. Touch-screen sensor 32 may be resistive, capacitive, or optically based. Pushbutton sensors may be used to detect the state of push buttons 34, which may include rockers. Input from the pushbutton sensors may be used to enact a home-key or on-off feature, control audio volume, turn microphone 36 on or off, etc.

FIGS. 1A and 1B show various other sensors of wearable electronic device 10. Such sensors include microphone 36, visible-light sensor 38, ultraviolet sensor 40, and ambient temperature sensor 42. Microphone 36 provides input to compute system 18 that may be used to measure the ambient sound level or receive voice commands from the wearer. Input from visible-light sensor 38, ultraviolet sensor 40, and ambient temperature sensor 42 may be used to assess aspects of the wearer's environment—i.e., the temperature, overall lighting level, and whether the wearer is indoors or outdoors.

FIGS. 1A and 1B show a pair of contact sensor modules 44A and 44B, which contact the wearer's skin when wearable electronic device 10 is worn. Contact sensor modules 44A and 44B may include independent or cooperating sensor elements, to provide a plurality of sensory functions. For example, contact sensor modules 44A and 44B may provide an electrical resistance and/or capacitance sensory function, which measures the electrical resistance and/or capacitance of the wearer's skin. Compute system 18 may use such input to assess whether or not wearable electronic device 10 is being worn, for instance. In some implementations, the sensory function may be used to determine how tightly wearable electronic device 10 is being worn. In the illustrated configuration, the separation between contact-sensor modules 44A and 44B provides a relatively long electrical path length, for more accurate measurement of skin resistance. In some examples, one or both of contact sensor modules 44A and 44B or an additional contact sensor module may provide measurement of the wearer's skin temperature. Arranged inside contact sensor module 44B in the illustrated configuration is optical heart rate sensor 46. The optical heart rate sensor may include an optical source and matched optical sensor to detect blood flow through the capillaries in the skin and thereby provide a measurement of the wearer's heart rate, blood oxygen level, blood glucose level, or other biomarkers with optical properties. Further details regarding the optical heart rate sensor, optical source, and optical sensor are provided with reference to FIG. 2.

Wearable electronic device 10 may also include motion sensing componentry, such as an accelerometer 48, gyroscope 50, and magnetometer 51. Accelerometer 48 and gyroscope 50 may furnish inertial and/or rotation rate data along three orthogonal axes as well as rotational data about the three axes, for a combined six degrees of freedom. This sensory data can be used to provide a pedometer/calorie-counting function, for example. Data from accelerometer 48 and gyroscope 50 may be combined with geomagnetic data from magnetometer 51 to further define the inertial and rotational data in terms of geographic orientation. Wearable electronic device 10 may also include a global positioning system (GPS) receiver 52 for determining the wearer's geographic location and/or velocity. In some configurations, the antenna of GPS receiver 52 may be relatively flexible and may extend into flexion regions 12.

Compute system 18, via the sensory functions described herein, is configured to acquire various forms of information about the wearer of wearable electronic device 10. Such information must be acquired and used with utmost respect for the wearer's privacy. Accordingly, the sensory functions may be enacted subject to opt-in participation of the wearer. In implementations where personal data is collected on wearable electronic device 10 and transmitted to a remote system for processing, that data may be anonymized. In other examples, personal data may be confined to wearable electronic device 10, and only non-personal, summary data transmitted to the remote system.

Figure 2:
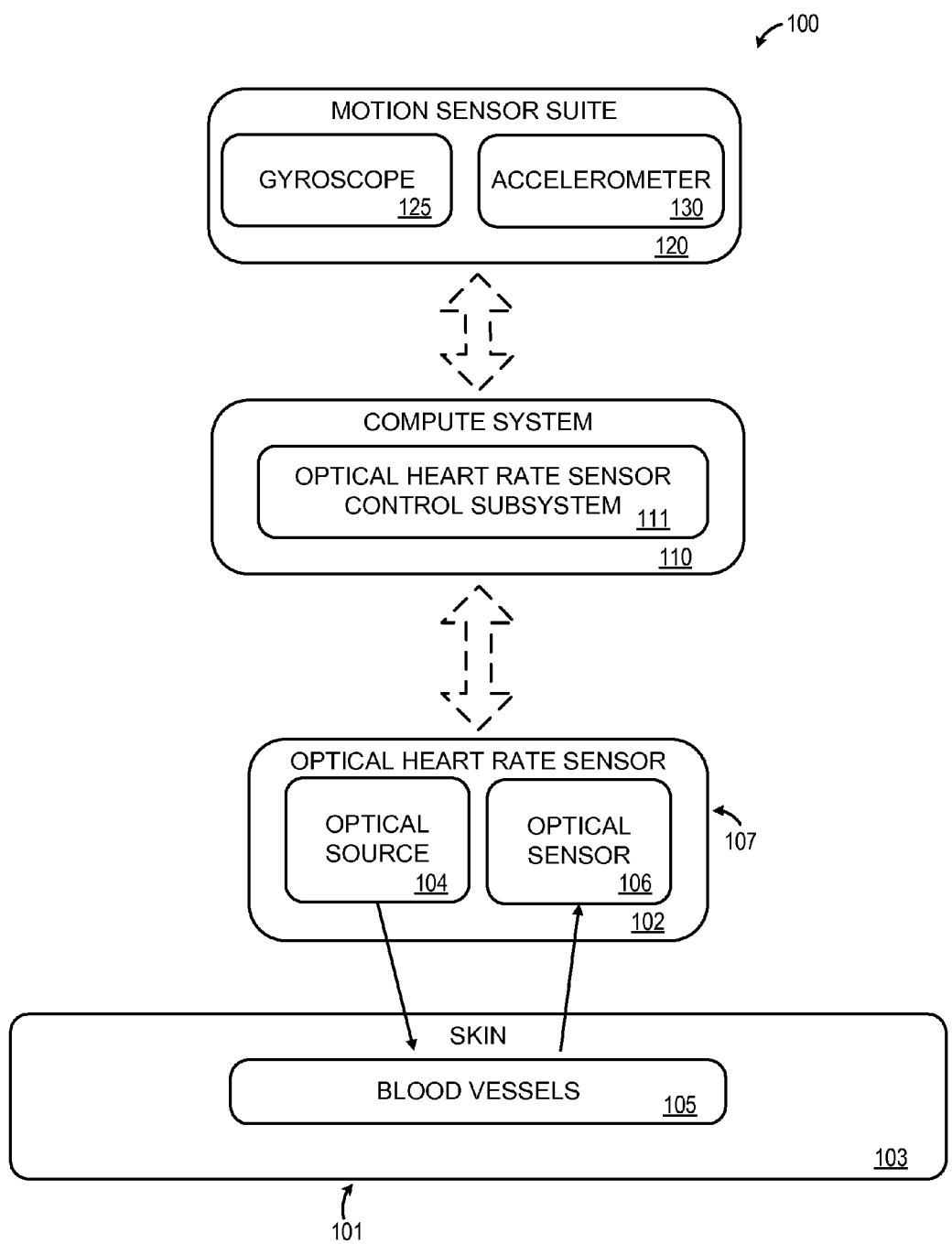
FIG. 2 schematically shows an example optical heart rate sensor that may be included in the wearable electronic device of FIGS. 1A-1B.

FIG. 2 shows a schematic depiction of a sensory-and-logic system 100 coupled to the wrist of a wearer 101 so that an optical heart rate sensor 102 is adjacent to the skin 103 of wearer 101. Optical heart rate sensor 102 comprises an optical source 104 configured to illuminate one or more blood vessels 105 through the skin of the user, and an optical sensor 106, configured to measure reflected illumination from the blood vessels. Optical source 104 may comprise one or more LED emitters, for example, while optical sensor 106 may comprise one or more photodiodes matched to detect light at frequencies that are based on the frequencies of light output by optical source 104.

Optical heart rate sensor 102 may be coupled within a housing 107 configured to promote contact between optical sensor 106 and skin 103, and further configured to block, filter, or otherwise limit ambient light from reaching optical sensor 106. In this way, the majority of light reaching optical sensor 106 may be light originating from optical source 104 that has reflected off of blood vessels 105 beneath skin 103. As an example, FIG. 1A shows a wearable electronic device 10 that is configured to position optical heart rate sensor 46 such that its optical source may illuminate capillaries located beneath the skin of the wearer's forearm while wearable electronic device 10 is worn by the wearer. In other configurations, optical heart rate sensor 102 may be positioned within a wearable electronic device such that optical source 104 illuminates a radial artery through the skin of the wearer while the wearable electronic device is being worn.

Alternatively, optical heart rate sensor 102 and its associated compute system 110 may be housed separately and configured to communicate via a communication suite. For example, optical heart rate sensor 102 may be included in a head set and configured to illuminate capillaries located in the wearer's ear lobe when the head set is worn, while compute system 110 resides within a wrist-worn computing device configured to communicate with the head set, via wireless communication, for example. Optical sensor 106 may be configured to sense light reflected off of blood vessels 105 located beneath the skin 103 of the wearer (e.g., wrist worn), or optical sensor 106 may be configured to sense light transmitted through blood vessels 105 located beneath the skin 103 of the wearer (e.g., ear worn).

Compute system 110 may comprise optical heart rate sensor control subsystem 111. Optical heart rate sensor control subsystem 111 may provide control signals to optical source 104 and optical sensor 106. Optical heart rate sensor control subsystem 111 may receive raw signals from optical sensor 106, and may further process the raw signals to determine heart rate, caloric expenditures, etc. Processed signals may be stored and output via compute system 110. Control signals sent to optical source 104 and optical sensor 106 may be based on signals received from optical sensor 106, one or more motion sensors included in motion sensor suite 120, ambient light sensors, information stored in compute system 110, input signals, etc.

The signal from optical sensor 106 may degrade in quality with increased motion, as wearer motion may change the optical properties of skin 103, tissues, and blood vessels 105 beneath optical sensor 106. Further, wearer motion may impact the movement of blood and other fluids through the wearer's tissue. As such, the signal output by optical sensor 106 may need to be filtered or otherwise adjusted based on wearer movement prior to determining a heart rate of the wearer. Sensory-and-logic system 100 may include motion sensor suite 120, which may be communicatively coupled to compute system 110. Signals from motion sensor suite 120 may be provided to optical heart rate control subsystem 111. Motion sensor suite 120 may include gyroscope 125 and accelerometer 130. Gyroscope 125 and accelerometer 130 may be three-axis motion sensors. Accordingly, gyroscope 125 and accelerometer 130 may record and transmit signal channels for each axis.

Figure 3:
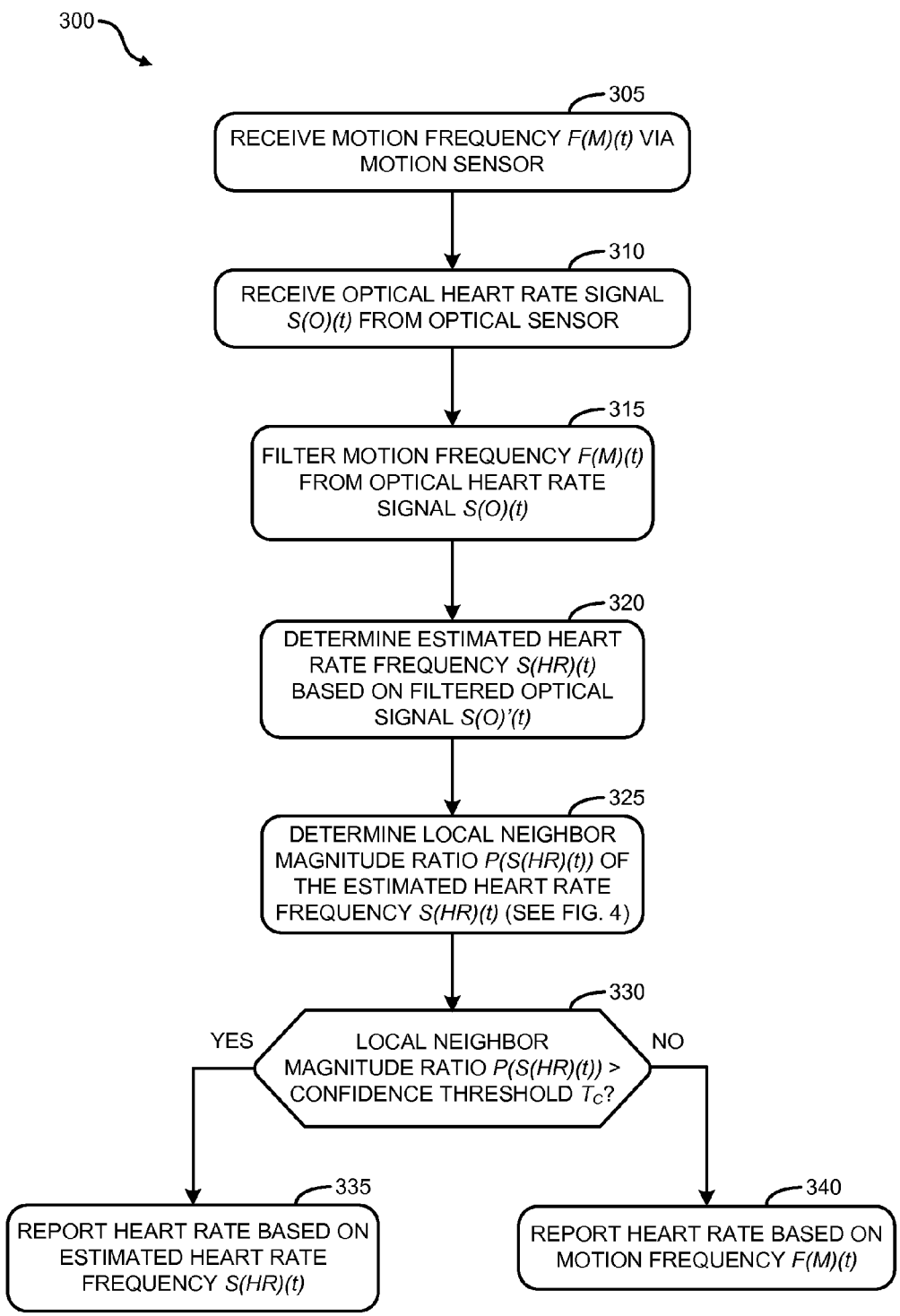
FIG. 3 shows a flow chart for an example method of reporting a heart rate based on an optical signal and a motion signal.

FIG. 3 shows an example method for an optical heart rate sensor in reporting a heart rate at a given time (t) based on an optical signal and a motion signal. At 305, method 300 includes receiving a motion frequency F(M)(t) via one or more motion sensors. The one or more motion sensors may comprise a gyroscope and/or an accelerometer, as nonlimiting examples. The gyroscope and/or accelerometer may be three-axis motion sensors. In those examples, the motion signal S(M)(t) output by the motion sensor may comprise a signal channel for each axis. As an example, a motion signal S(M)(t) may be received from the one or more motion sensors, and a motion frequency F(M)(t) may be estimated based on the motion signal S(M)(t). At 310, method 300 includes receiving an optical signal S(O)(t) from an optical sensor. The optical signal S(O)(t) may indicate reflected illumination from one or more blood vessels illuminated by an optical source through a user's skin.

At 315, method 300 includes filtering the motion frequency F(M)(t) from the optical heart rate signal S(O)(t). An amount of motion frequency filtering may remain constant with changing motion frequency, rather than adaptively or dynamically adjusting the amount of motion frequency filtering based on the magnitude of the motion frequency. Further, the amount of motion frequency filtering may remain constant with changing heart rate frequency. In one example, a filtered optical signal S(O)'(t) may be determined based on the algorithm:

$$S(O)'(t)=S(O)(t)-k*S(O)(t-1/F(M)(t))$$

In this example algorithm, k is a variable set such that 0<k<1, where an increased value for k corresponds with a greater amount of motion signal filtering, and thus a more aggressive application of motion compensation. For example, an aggressive motion filtering algorithm may include a value for k of 0.9. Filtering the optical signal S(O)(t) based on the motion frequency F(M(t)) may include applying a comb filter to the optical signal, although other types of filters or methods of signal processing may be used to remove the motion frequency from the optical signal in addition to or as an alternative to the comb filter, such as infinite impulse response filters or notch filters. In some examples, one or more parameters of the comb filter may be adjusted based on a recent motion frequency while maintaining the amount of motion signal filtering. For example, as the motion frequency and heart rate frequency change over time, the harmonic frequencies of the motion signal that are similar to the heart rate frequency may change. The distribution of frequency suppression applied in motion compensation may thus be dynamically adjusted while the overall amount of motion frequency filtering remains constant.

Continuing at 320, method 300 includes determining an estimated heart rate frequency S(HR)(t) (e.g. in BPM) based on the filtered optical signal S(O)'(t). The filtered optical signal S(O)'(t) may be analyzed in real time. As a non-limiting example, the filtered optical signal S(O)'(t) may be detrended (i.e., a mean or best fit line subtracted from the filtered optical signal). An estimated heart rate frequency S(HR)(t) may then be determined based on zero-crossing events of the detrended filtered optical signal. A zero-axis may be determined and applied to the detrended filtered optical signal. Each heart beat comprises two zero-crossing events, a negative-to-positive zero-crossing event, and a positive-to-negative zero-crossing event. As such, the length of time between alternating zero-crossing events, may be used to determine a heart rate. In some examples, heart rate may be determined based on amplitude peaks in addition to or as an alternative to zero crossing events. The length of time between consecutive amplitude peaks may be used to determine a heart rate of the user. Other methods of determining heart rate from a processed optical signal may be used in addition to or as an alternative to the described methods without departing from the scope of this disclosure.

At 325, method 300 includes determining a local neighbor magnitude ratio P(S(HR)(t)) of the estimated heart rate frequency S(HR)(t). The local neighbor magnitude ratio P(S(HR)(t)) may represent a probability that the estimated heart rate frequency S(HR)(t) is representative of the actual heart rate frequency when compared to neighboring frequencies.

Figure 4:
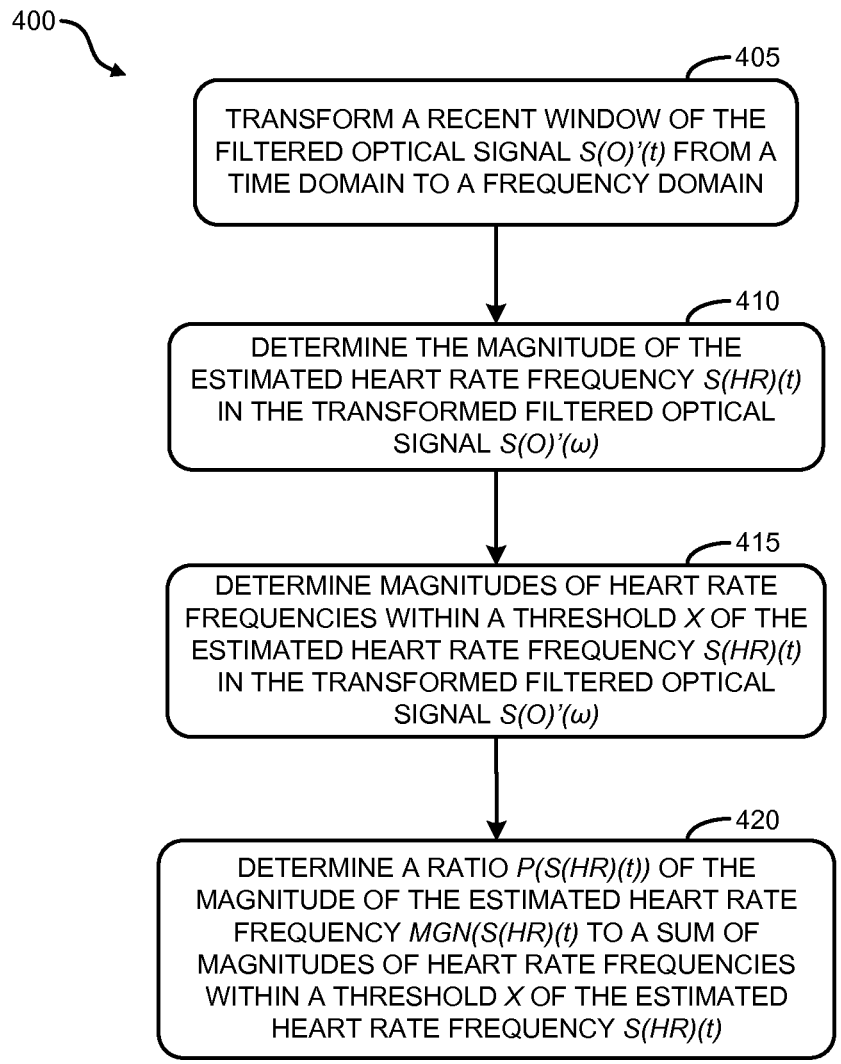
FIG. 4 shows a flow chart for an example method of determining a local neighbor magnitude ratio for an estimated heart rate frequency.

Turning briefly to FIG. 4, a flow chart is depicted for an example method 400 of determining a local neighbor magnitude ratio for an estimated heart rate frequency, for example, as determined at 325 of FIG. 3. At 405, method 400 includes transforming a recent window of the filtered optical signal S(O)'(t) from a time domain to a frequency domain. For example, a recent window of the filtered optical signal S(O)'(t) may be subject to a fast Fourier transform (FFT) to yield a transformed filtered optical signal S(O)'(ω) The recent window of the filtered optical signal S(O)'(t) may comprise a most recent five second window, but may comprise a larger or smaller window of data in some examples.

At 410, method 400 includes determining the magnitude of the estimated heart rate frequency MGN(S(HR)(t)) within the transformed filtered optical signal S(O)'(ω). At 415, method 400 includes determining magnitudes of heart rate frequencies within a threshold X of the estimated heart rate frequency (e.g., (S(HR)(t)±X BPM) in the transformed filtered optical signal S(O)'(ω). For example, the threshold X may be set to 30 beats per minute. Accordingly, the magnitudes of each heart rate frequency within 30 BPM of the estimated heart rate frequency S(HR)(t) may be determined.

At 420, method 400 includes determining a ratio P(S(HR)(t)) of a magnitude of the estimated heart rate frequency MGN(S(HR)(t) to a sum of magnitudes of heart rate frequencies within a threshold of the estimated heart rate frequency (e.g., the local neighbor magnitude ratio). For example, a local neighbor magnitude ratio P(S(HR)(t)) for the estimated heart rate frequency (S(HR)(t)) may be determined based on the algorithm:

$$P(S(HR)(t)) = \frac{MGN(S(HR)(t))}{\sum [MGN(S(HR)(t) - X \text{ bpm}), \ldots, MGN(S(HR)(t) + X \text{ bpm})]}$$

Where MGN(y) is the magnitude at y BPM in the transformed filtered optical signal (S(O)'(ω)).

Returning to FIG. 3, at 330, method 300 includes determining whether the local neighbor magnitude ratio P(S(HR)(t)) is greater than a confidence threshold $T_C$. For example, the confidence threshold may be set to 0.2, though in other scenarios, the threshold may be set higher or lower. In some examples, the confidence threshold may be dynamically adjusting based on the motion frequency and/or the estimated heart rate frequency. For example, if the optical heart rate sensor samples heart rate at a constant frequency, the resolution of the optical heart rate signal S(O)(t) will decrease as heart rate increases. Accordingly, confidence threshold $T_C$ may be decreased inversely proportionate to heart rate and/or decreased proportionate to the resolution of the optical heart rate signal S(O)(t).

If the local neighbor magnitude ratio P(S(HR)(t)) is greater than the confidence threshold $T_C$, method 300 proceeds to 335, and includes reporting a heart rate based on the estimated heart rate frequency S(HR)(t). Reporting a heart rate based on the estimated heart rate frequency S(HR)(t) may comprise recording the estimated heart rate frequency in a buffer of recent estimated heart rate frequencies, and determining a current heart rate based on the updated buffer of recent estimated heart rate frequencies. In some examples, the estimated heart rate frequency S(HR)(t) may be processed based on recent estimated heart rate frequencies before being recorded. For example, if the estimated heart rate frequency S(HR)(t) is more than a threshold different from a recent estimated heart rate frequency, and/or is more than a threshold different from a current heart rate, the estimated heart rate frequency S(HR)(t) may be adjusted to a value within the threshold. Once determined, the current heart rate may be stored in memory, and may be indicated to a wearer of the optical sensor via a user interface.

If the local neighbor magnitude ratio P(S(HR)(t)) is less than the confidence threshold $T_C$, method 300 proceeds to 340, and includes reporting a heart rate based on the motion frequency F(M)(t), but not based on the estimated heart rate frequency S(HR)(t). For example, the heart rate may be recorded as 2*(F(M)(t)). As per examples wherein the estimated heart rate frequency S(HR)(t) is reported, reporting a heart rate based on the motion frequency F(M)(t) may include further signal processing and/or adjustment prior to determining a current heart rate.

FIG. 5A shows an example plot 500 of a filtered optical signal that may be derived by filtering a motion frequency from an optical heart rate signal. Plot 500 includes signal trace 501, indicating the amplitude of the filtered optical signal over a five second data window. The repetitive nature of the heart beating yields a periodic plot when illuminated by an optical source. Each successive heart beat yields an amplitude peak, and the length of time between successive amplitude peaks is representative of heart rate frequency. However, as the amplitude of the peaks may change from beat to beat, a zero-axis 505 may be determined and applied to signal trace 501. An estimated heart rate frequency may thus be determined based on the length of time between alternating zero-crossing events.

FIG. 5A further shows an example plot 530, showing an example transformation of signal trace 501 from the time domain to the frequency domain. Frequency 531 represents an estimated heart rate derived from the filtered optical signal. Plot 530 also includes neighboring frequencies 533, comprising heart rate frequencies that are within a threshold below estimated heart rate frequency 531, and neighboring frequencies 535, comprising heart rate frequencies that are within a threshold above estimated heart rate frequency 531. In this example, the threshold is set at 12 BPM.

As shown in plot 530, the distribution of frequency magnitudes around estimated heart rate frequency 531 is a relatively normal distribution with a sharp peak centered at frequency 531. Such a distribution may be representative of a filtered optical signal having a local neighbor magnitude ratio P greater than a confidence threshold. In this example, P≈0.24.

In contrast to signal trace 501, which has a relatively high signal-to-noise ratio, FIG. 5B shows an example plot 550 including signal trace 551, which has a relatively low signal-to-noise ratio. Signal trace 551 indicates the amplitude of the filtered optical signal over a five second data window. Zero-crossing events of signal trace 551 around zero-axis 555 may be used to determine an estimated heart rate frequency.

Plot 570 shows an example transformation of signal trace 551 from the time domain to the frequency domain, wherein frequency 571 represents an estimated heart rate derived from the filtered optical signal, neighboring frequencies 573 comprise heart rate frequencies that are within a threshold (12 BPM) below estimated heart rate frequency 571, and neighboring frequencies 575 comprise heart rate frequencies that are within a threshold (12 BPM) above estimated heart rate frequency 571.

As shown in plot 570, the distribution of frequency magnitudes around estimated heart rate frequency 571 is more random than the distribution shown in plot 530, and several of the neighboring frequencies 573 and 575 have similar magnitudes to estimated heart rate frequency 571. Such a distribution may be representative of a filtered optical signal having a local neighbor magnitude ratio P less than a confidence threshold. In this example, P≈0.08.

Figure 6A:
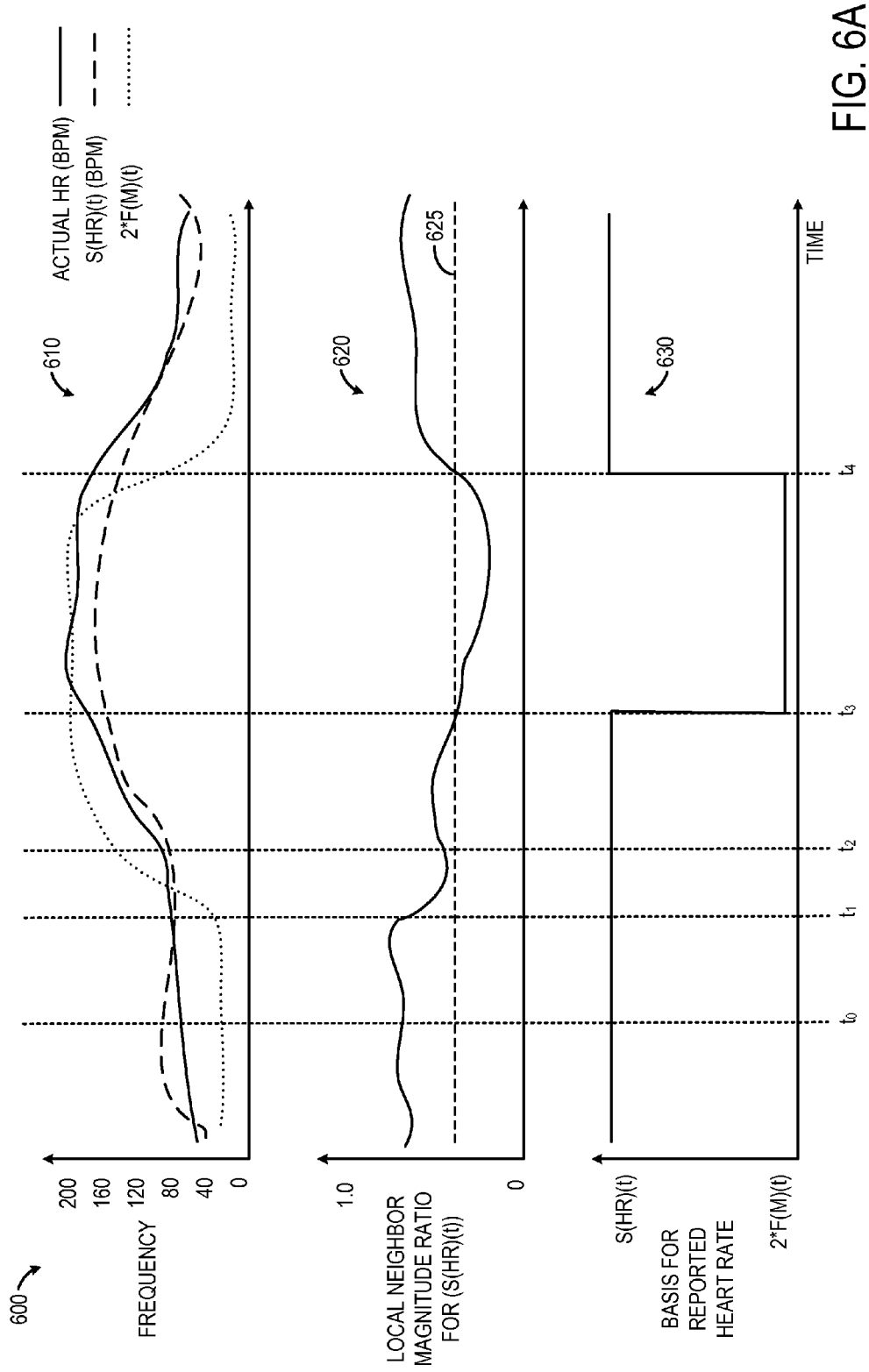
FIGS. 6A & 6B show example timelines for reporting heart rate based on an optical signal and a motion signal.

FIG. 6A depicts an example timeline 600 for reporting a heart rate based on an optical signal and a motion signal received for a typical athlete wearing an optical heart rate monitor. Timeline 600 includes plot 610, indicating signal frequencies over time. Plot 610 depicts actual heart rate frequency in beats per minute (solid line), estimated heart rate frequency in beats per minute (dashed line) and adjusted estimated motion frequency (dotted line). The estimated heart rate frequency S(HR)(t) is determined from an optical signal S(O)(t) and a motion signal S(M)(t) as described with reference to FIG. 3. The amount of the motion signal filtering applied to the optical signal remains constant throughout timeline 600. The adjusted estimated motion frequency is determined as 2x a motion frequency F(M)(t) estimated from a motion signal S(M)(t), also as described with reference to FIG. 3. Timeline 600 further includes plot 620, indicating a local neighbor magnitude ratio for the estimated heart rate frequency S(HR)(t) derived from the filtered optical signal S(O)'(t) when transformed into the frequency domain S(O)'(ω). Plot 620 includes confidence threshold 625. Timeline 600 further includes plot 630, indicating whether reported heart rate is based on the estimated heart rate frequency S(HR)(t) or the adjusted estimated motion frequency 2*F(M)(t) over time.

At time $t_0$, the local neighbor magnitude ratio for the estimated heart rate frequency S(HR)(t) is above confidence threshold 625, as shown in plot 620. Accordingly, the reported heart rate is based on the estimated heart rate. At time $t_1$, the adjusted motion frequency begins to increase, as shown in plot 610. This causes the local neighbor magnitude ratio to decrease from time $t_1$ to time $t_2$, as the harmonic motion frequencies are filtered from the optical signal, however the local neighbor magnitude ratio remains above confidence threshold 625.

In this example the heart rate increases with increased motion frequency, until time $t_3$, when the actual heart rate frequency is similar to the adjusted motion frequency. The estimated heart rate frequency S(HR)(t), which is determined following aggressively filtering the motion frequency F(M)(t) out of the optical signal S(O)(t), thus becomes less similar to the actual heart rate, and the local neighbor magnitude ratio decreases below confidence threshold 625. Accordingly, the reported heart rate switches to being based on the adjusted estimated motion frequency, as shown in plot 630. The adjusted estimated motion frequency is used as a proxy for heart rate until time $t_4$, when the motion frequency has decreased, and the local neighbor magnitude ratio increases above confidence threshold 625. Accordingly, at time $t_4$, the reported heart rate is again based on the estimated heart rate.

Figure 6B:
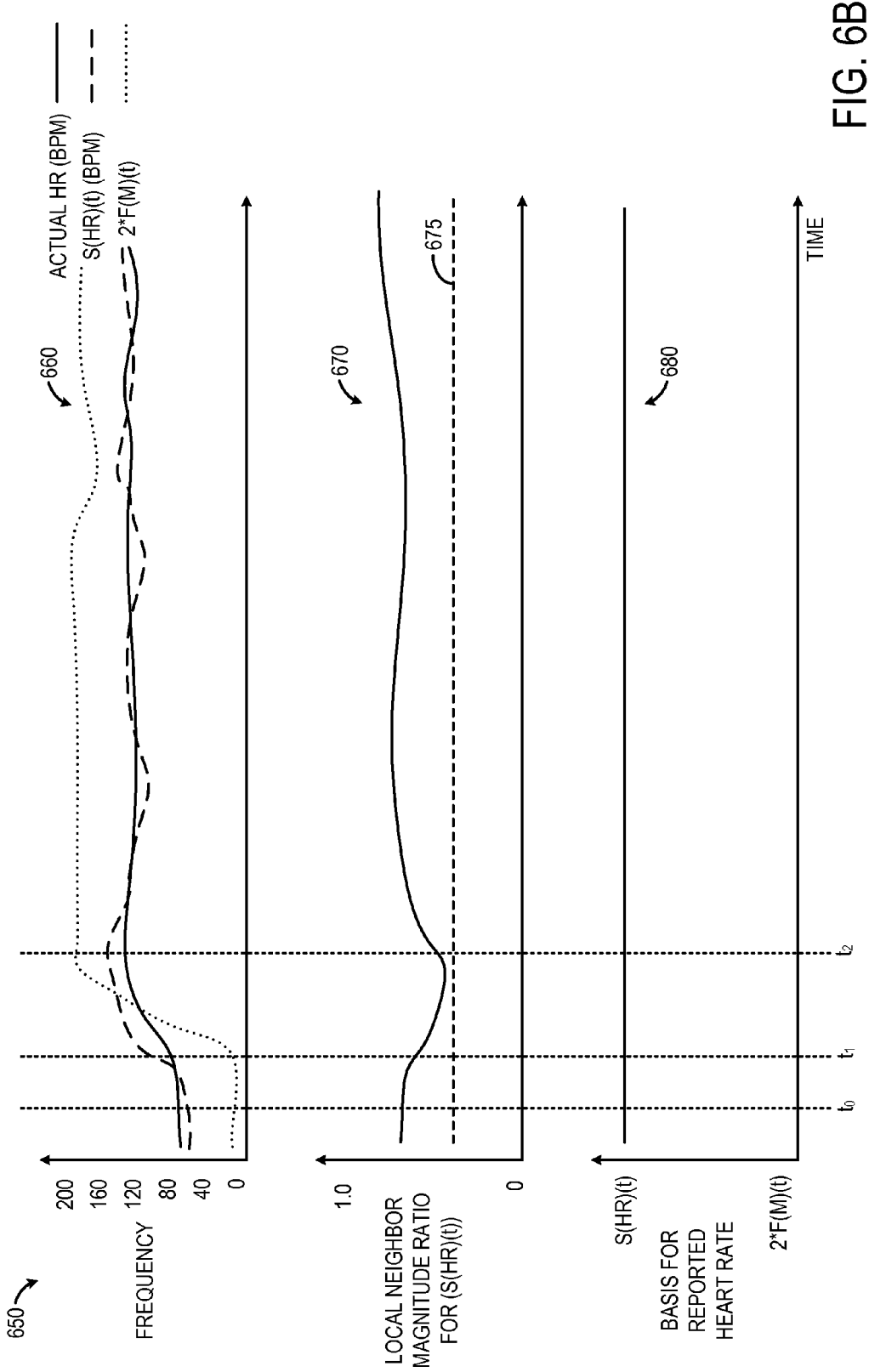

FIG. 6B depicts an example timeline 650 for determining heart rate based on an optical signal and a motion signal received from a high-level runner wearing an optical heart rate monitor. Timeline 650 includes plot 660, indicating signal frequencies over time. Including actual heart rate frequency in BPM (solid line), estimated heart rate frequency in BPM (dashed line) and adjusted estimated motion frequency (dotted line). Parameters for estimated heart rate frequency S(HR)(t) and adjusted estimated motion frequency 2*F(M)(t) are the same as described with reference to FIG. 6A. Timeline 650 further includes plot 670, indicating a local neighbor magnitude ratio for the estimated heart rate frequency S(HR)(t). Plot 670 includes confidence threshold 675. Timeline 650 further includes plot 680, indicating whether reported heart rate is based on the estimated heart rate frequency S(HR)(t) or the adjusted estimated motion frequency 2*F(M)(t) over time.

At time $t_0$, the local neighbor magnitude ratio for the estimated heart rate frequency S(HR)(t) is above confidence threshold 675, as shown in plot 670. Accordingly, the reported heart rate is based on the estimated heart rate. At time $t_1$, the adjusted motion frequency begins to increase, causing the local neighbor magnitude ratio to decrease from time $t_1$ to time $t_2$, although the local neighbor magnitude ratio remains above confidence threshold 675. At time $t_2$, the adjusted motion frequency reaches a relatively steady-state frequency. For the high-level runner, the actual heart rate frequency remains well below the adjusted motion frequency from time $t_2$ onward. As such, the estimated heart rate frequency S(HR)(t) remains representative of the actual heart rate frequency, the local neighbor magnitude ratio remains above confidence threshold 675, and the reported heart rate continues to be based on the estimated heart rate frequency S(HR)(t).

In some examples, the optical heart rate sensor may be selectively activated, while the motion sensors are constantly, or at least more frequently, activated when the wearable electronic device is worn. While the optical heart rate sensor is off, and thus no optical signal is received, heart rate may be estimated and reported based on a last reliable heart rate signal, motion signals received from the motion sensors (and/or the motion frequencies derived from the motion signals), utilizing one or more algorithms to correlate changes in the relative amount of motion with expected changes in heart rate. For example, if a wearer is moving below a threshold amount, it may be assumed that their heart rate will remain relatively stable. This may allow the wearable electronic device to save power by selectively de-activating the optical heart rate sensor (and/or reducing the frequency of optical heart rate sensor activation) while still reporting a reasonably accurate heart rate. The optical heart rate sensor may be occasionally activated to confirm the reported heart rates, or may be activated in response to a change in motion frequency above a threshold, and/or other recognized conditions.

Actively reporting the heart rate based on motion frequency when the estimated heart rate frequency is unreliable or unlikely to be representative of the actual heart rate may thus provide an additional level of power savings, as the optical heart rate sensor may be deactivated or activated in a reduced power mode responsive to a local neighbor magnitude ratio decreasing below a confidence threshold. The reactivation or return to full power mode of the optical heart rate sensor may be indicated responsive to changes in motion frequency, and/or other parameters that indicate whether the local neighbor magnitude ratio is likely to be greater than (and/or approaching) the confidence threshold.

As evident from the foregoing description, the methods and processes described herein may be tied to a sensory-and-logic system of one or more machines. Such methods and processes may be implemented as a computer-application program or service, an application-programming interface (API), a library, firmware, and/or other computer-program product. FIGS. 1A and 1B show one, non-limiting example of a sensory-and-logic system to enact the methods and processes described herein. However, these methods and process may also be enacted on sensory-and-logic systems of other configurations and form factors, as shown schematically in FIG. 7.

Figure 7:
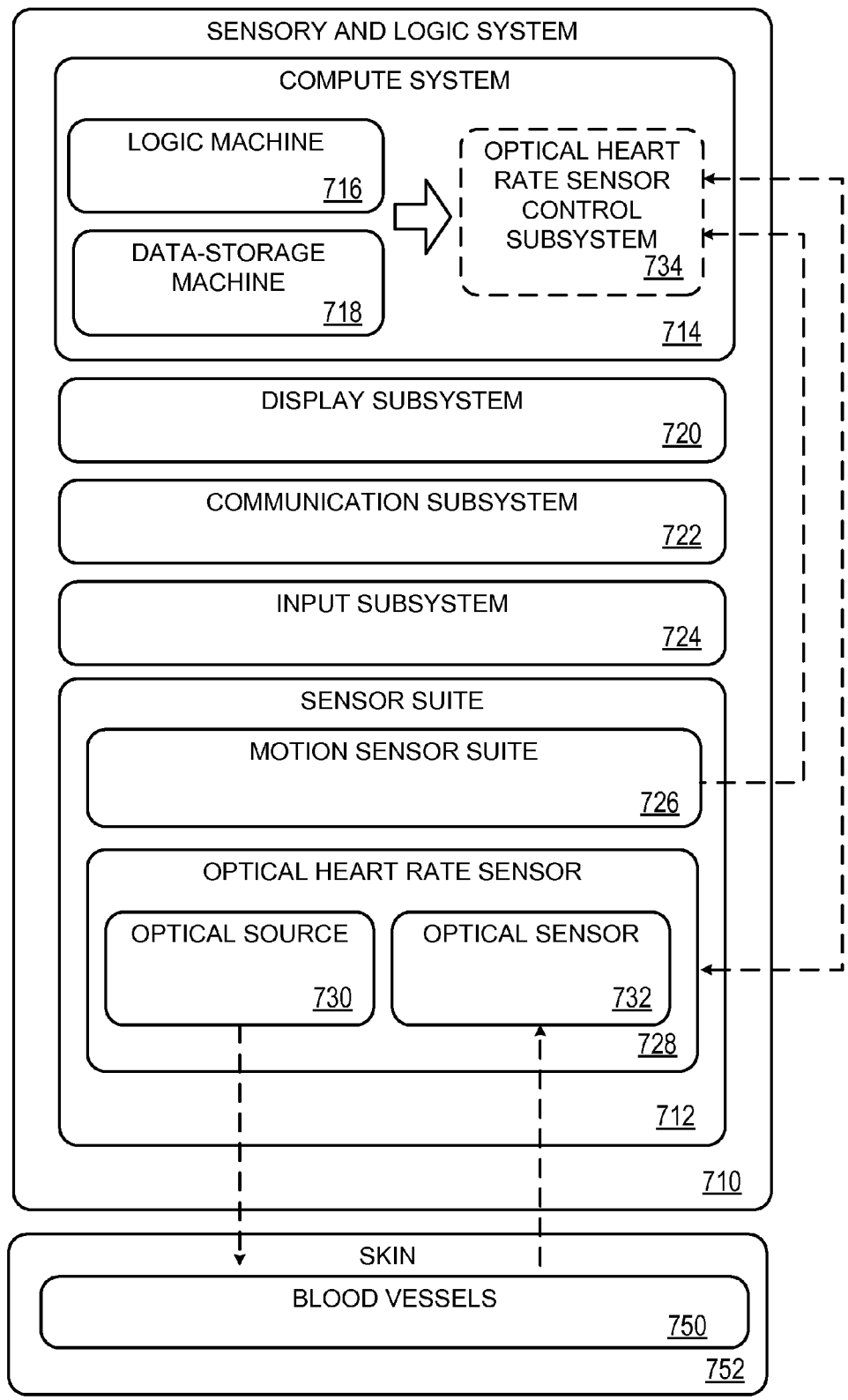
FIG. 7 schematically shows a sensory-and-logic system usable to report a heart rate based on an optical signal and a motion signal during predetermined conditions.

FIG. 7 schematically shows a form-agnostic sensory-and-logic system 710 that includes a sensor suite 712 operatively coupled to a compute system 714. The compute system includes a logic machine 716 and a data-storage machine 718. The compute system is operatively coupled to a display subsystem 720, a communication subsystem 722, an input subsystem 724, and/or other components not shown in FIG. 7.

Logic machine 716 includes one or more physical devices configured to execute instructions. The logic machine may be configured to execute instructions that are part of one or more applications, services, programs, routines, libraries, objects, components, data structures, or other logical constructs. Such instructions may be implemented to perform a task, implement a data type, transform the state of one or more components, achieve a technical effect, or otherwise arrive at a desired result.

Logic machine 716 may include one or more processors configured to execute software instructions. Additionally or alternatively, the logic machine may include one or more hardware or firmware logic machines configured to execute hardware or firmware instructions. Processors of the logic machine may be single-core or multi-core, and the instructions executed thereon may be configured for sequential, parallel, and/or distributed processing. Individual components of a logic machine optionally may be distributed among two or more separate devices, which may be remotely located and/or configured for coordinated processing. Aspects of a logic machine may be virtualized and executed by remotely accessible, networked computing devices in a cloud-computing configuration.

Data-storage machine 718 includes one or more physical devices configured to hold instructions executable by logic machine 716 to implement the methods and processes described herein. When such methods and processes are implemented, the state of the data-storage machine may be transformed—e.g., to hold different data. The data-storage machine may include removable and/or built-in devices; it may include optical memory (e.g., CD, DVD, HD-DVD, Blu-Ray Disc, etc.), semiconductor memory (e.g., RAM, EPROM, EEPROM, etc.), and/or magnetic memory (e.g., hard-disk drive, floppy-disk drive, tape drive, MRAM, etc.), among others. The data-storage machine may include volatile, nonvolatile, dynamic, static, read/write, read-only, random-access, sequential-access, location-addressable, file-addressable, and/or content-addressable devices.

Data-storage machine 718 includes one or more physical devices. However, aspects of the instructions described herein alternatively may be propagated by a communication medium (e.g., an electromagnetic signal, an optical signal, etc.) that is not held by a physical device for a finite duration.

Aspects of logic machine 716 and data-storage machine 718 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

Display subsystem 720 may be used to present a visual representation of data held by data-storage machine 718. This visual representation may take the form of a graphical user interface (GUI). As the herein described methods and processes change the data held by the storage machine, and thus transform the state of the storage machine, the state of display subsystem 720 may likewise be transformed to visually represent changes in the underlying data. Display subsystem 720 may include one or more display subsystem devices utilizing virtually any type of technology. Such display subsystem devices may be combined with logic machine 716 and/or data-storage machine 718 in a shared enclosure, or such display subsystem devices may be peripheral display subsystem devices. Display 20 of FIGS. 1A and 1B is an example of display subsystem 720.

Communication subsystem 722 may be configured to communicatively couple compute system 714 to one or more other computing devices. The communication subsystem may include wired and/or wireless communication devices compatible with one or more different communication protocols. As non-limiting examples, the communication subsystem may be configured for communication via a wireless telephone network, a local- or wide-area network, and/or the Internet. Communication suite 24 of FIGS. 1A and 1B is an example of communication subsystem 722.

Input subsystem 724 may comprise or interface with one or more user-input devices such as a keyboard, mouse, touch screen, or game controller. In some embodiments, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity. Touch-screen sensor 32 and push buttons 34 of FIGS. 1A and 1B are examples of input subsystem 724.

Sensor suite 712 may include one or more different sensors—e.g., a touch-screen sensor, push-button sensor, microphone, visible-light sensor, ultraviolet sensor, ambient-temperature sensor, contact sensors, and/or GPS receiver—as described above with reference to FIGS. 1A and 1B. Sensor suite 712 may include motion sensor suite 726. Motion sensor suite 726 may include one or more of an accelerometer, gyroscope, magnetometer, or other suitable motion detectors. Sensor suite 712 may further include optical heart rate sensor 728. As described herein, optical heart rate sensor 728 may include optical source 730 and optical sensor 732. Compute system 714 may include optical heart rate control subsystem 734, which may be communicatively coupled to logic machine 716 and data-storage machine 718. Optical source 730 may comprise one or more LED emitters, for example, while optical sensor 732 may comprise one or more photodiodes matched to detect light at frequencies that are based on the frequencies of light output by the optical source. Optical source 730 may be configured to illuminate one or more blood vessels 750 through the skin 752 of the user, and optical sensor 732 may be configured to measure illumination reflected from or transmitted through blood vessels 750.

Optical heart rate control subsystem 734 may receive raw signals from optical sensor 732, and may further process the raw signals to determine heart rate, caloric expenditures, etc. Processed signals may be stored and output via compute system 714. Control signals sent to optical source 730 and optical sensor 732 may be based on signals received from optical sensor 732, signals derived from sensor suite 712, information stored in data-storage machine 718, input received from communication subsystem 722, input received from input subsystem 724, etc.

In one example implementation, a method of optical heart rate sensing comprises receiving a motion frequency via a motion sensor; receiving an optical signal from an optical sensor; filtering the motion frequency from the optical signal; determining an estimated heart rate frequency based on the filtered optical signal; and reporting a heart rate based on the motion frequency, but not based on the estimated heart rate frequency responsive to a local neighbor magnitude ratio of the estimated heart rate frequency being less than a confidence threshold. In one example implementation that optionally may be combined with any of the features described herein, the method further comprises reporting a heart rate based on the estimated heart rate frequency responsive to the local neighbor magnitude ratio of the estimated heart rate frequency being greater than the confidence threshold. In one example implementation that optionally may be combined with any of the features described herein, the method further comprises dynamically adjusting the confidence threshold based on the estimated heart rate frequency. In one example implementation that optionally may be combined with any of the features described herein, the local neighbor magnitude ratio of the estimated heart rate frequency comprises a ratio of a magnitude of the estimated heart rate frequency to a sum of magnitudes of heart rate frequencies within a threshold of the estimated heart rate frequency. In one example implementation that optionally may be combined with any of the features described herein the magnitudes of heart rate frequencies within a threshold of the estimated heart rate frequency include magnitudes of heart rate frequencies within 30 beats per minute of the estimated heart rate frequency. In one example implementation that optionally may be combined with any of the features described herein, the method further comprises transforming a recent window of the filtered optical signal from a time domain to a frequency domain; determining the magnitude of the estimated heart rate frequency based on the transformed filtered optical signal; and determining magnitudes of heart rate frequencies within a threshold of the estimated heart rate frequency based on the transformed filtered optical signal. In one example implementation that optionally may be combined with any of the features described herein, the recent window of the filtered optical signal is a recent five second window. In one example implementation that optionally may be combined with any of the features described herein, an amount of motion signal filtering remains constant with changing motion frequency. In one example implementation that optionally may be combined with any of the features described herein, filtering the optical signal based on the motion frequency includes applying a comb filter to the optical signal. In one example implementation that optionally may be combined with any of the features described herein, filtering the optical signal based on the motion frequency further includes adjusting one or more parameters of the comb filter based on a recent motion frequency while maintaining the amount of motion signal filtering.

In another example implementation, an optical heart rate sensor comprises an optical source configured to illuminate one or more blood vessels through a user's skin; an optical sensor configured to measure illumination from the one or more blood vessels; one or more motion sensors; and a storage machine holding instructions executable by a logic machine to receive an optical signal from the optical sensor; receive a motion signal from the one or more motion sensors; determine a motion frequency based on the motion signal; filter the motion frequency from the optical signal; determine an estimated heart rate frequency based on the filtered optical signal; report a heart rate based on the motion frequency, but not based on the estimated heart rate frequency, responsive to a local neighbor magnitude ratio of the estimated heart rate frequency being less than a confidence threshold. In one example implementation, that optionally may be combined with any of the features described herein, the local neighbor magnitude ratio of the estimated heart rate frequency comprises a ratio of a magnitude of the estimated heart rate frequency to a sum of magnitudes of heart rate frequencies within a threshold of the estimated heart rate frequency. In one example implementation, that optionally may be combined with any of the features described herein, the storage machine further holds instructions executable by a logic machine to transform a recent window of the filtered optical signal from a time domain to a frequency domain; determine the magnitude of the estimated heart rate frequency based on the transformed filtered optical signal; and determine magnitudes of heart rate frequencies within a threshold of the estimated heart rate frequency based on the transformed filtered optical signal. In one example implementation that optionally may be combined with any of the features described herein, the recent window of the filtered optical signal is a recent five second window. In one example implementation, that optionally may be combined with any of the features described herein, an amount of motion signal filtering remains constant with changing motion frequency.

In another example implementation, a method of optical heart rate sensing comprises receiving a motion frequency via a motion sensor; receiving an optical signal from an optical sensor; filtering the motion frequency from the optical signal with an amount of filtering that is independent of the motion frequency; determining an estimated heart rate frequency based on the filtered optical signal; determining a probability that the estimated heart rate frequency is the current heart rate frequency; and reporting a heart rate based on the estimated heart rate frequency responsive to the probability that the estimated heart rate frequency is the current heart rate frequency being greater than a confidence threshold. In one example implementation, that optionally may be combined with any of the features described herein filtering the optical signal based on the motion frequency includes applying a comb filter to the optical signal. In one example implementation, that optionally may be combined with any of the features described herein filtering the optical signal based on the motion frequency further includes adjusting one or more parameters of the comb filter based on a recent motion frequency while maintaining the amount of filtering. In one example implementation, that optionally may be combined with any of the features described herein determining a probability that the estimated heart rate frequency is the current heart rate frequency includes: transforming a recent window of the filtered optical signal from a time domain to a frequency domain; determining the magnitude of the estimated heart rate frequency based on the transformed filtered optical signal; and determining magnitudes of heart rate frequencies within a threshold of the estimated heart rate frequency based on the transformed filtered optical signal. In one example implementation, that optionally may be combined with any of the features described herein, the method further comprises determining a local neighbor magnitude ratio of the filtered optical signal comprising a ratio of the magnitude of the estimated heart rate frequency to a sum of magnitudes of heart rate frequencies within a threshold of the estimated heart rate frequency; and comparing the local neighbor magnitude ratio to the confidence threshold.

The configurations and approaches described herein are exemplary in nature, and that these specific implementations or examples are not to be taken in a limiting sense, because numerous variations are feasible. The specific routines or methods described herein may represent one or more processing strategies. As such, various acts shown or described may be performed in the sequence shown or described, in other sequences, in parallel, or omitted.

The subject matter of this disclosure includes all novel and non-obvious combinations and sub-combinations of the various processes, systems and configurations, and other features, functions, acts, and/or properties disclosed herein, as well as any and all equivalents thereof.

The invention claimed is:

1. A method of optical heart rate sensing, comprising:
receiving a motion frequency via a motion sensor;
receiving an optical signal from an optical sensor;
filtering the motion frequency from the optical signal;
determining an estimated heart rate frequency based on the filtered optical signal;
reporting a heart rate based on the motion frequency, but not based on the estimated heart rate frequency responsive to a local neighbor magnitude ratio of the estimated heart rate frequency being less than a confidence threshold; and
reporting a heart rate based on the estimated heart rate frequency responsive to the local neighbor magnitude ratio of the estimated heart rate frequency being greater than the confidence threshold.

2. The method of claim 1, further comprising:
dynamically adjusting the confidence threshold based on the estimated heart rate frequency.

3. The method of claim 1, wherein the local neighbor magnitude ratio of the estimated heart rate frequency comprises a ratio of a magnitude of the estimated heart rate frequency to a sum of magnitudes of heart rate frequencies within a threshold of the estimated heart rate frequency.

4. The method of claim 3, wherein the magnitudes of heart rate frequencies within a threshold of the estimated heart rate frequency include magnitudes of heart rate frequencies within 30 beats per minute of the estimated heart rate frequency.

5. The method of claim 3, further comprising:
transforming a recent window of the filtered optical signal from a time domain to a frequency domain;
determining the magnitude of the estimated heart rate frequency based on the transformed filtered optical signal; and
determining magnitudes of heart rate frequencies within a threshold of the estimated heart rate frequency based on the transformed filtered optical signal.

6. The method of claim 5, wherein the recent window of the filtered optical signal is a recent five second window.

7. The method of claim 1, wherein an amount of motion signal filtering remains constant with changing motion frequency.

8. The method of claim 7, wherein filtering the optical signal based on the motion frequency includes applying a comb filter to the optical signal.

9. The method of claim 8, wherein filtering the optical signal based on the motion frequency further includes:
adjusting one or more parameters of the comb filter based on a recent motion frequency while maintaining the amount of motion signal filtering.

10. An optical heart rate sensor, comprising:
an optical source configured to illuminate one or more blood vessels through a user's skin;
an optical sensor configured to measure illumination from the one or more blood vessels;
one or more motion sensors; and
a storage machine holding instructions executable by a logic machine to:
receive an optical signal from the optical sensor;
receive a motion signal from the one or more motion sensors;
determine a motion frequency based on the motion signal;
filter the motion frequency from the optical signal;
determine an estimated heart rate frequency based on the filtered optical signal;
report a heart rate based on the motion frequency, but not based on the estimated heart rate frequency, responsive to a local neighbor magnitude ratio of the estimated heart rate frequency being less than a confidence threshold; and
report a heart rate based on the estimated heart rate frequency responsive to the local neighbor magnitude ratio of the estimated heart rate frequency being greater than the confidence threshold.

11. The optical heart rate sensor of claim 10, wherein the local neighbor magnitude ratio of the estimated heart rate frequency comprises a ratio of a magnitude of the estimated heart rate frequency to a sum of magnitudes of heart rate frequencies within a threshold of the estimated heart rate frequency.

12. The optical heart rate sensor of claim 11, wherein the storage machine further holds instructions executable by a logic machine to:
transform a recent window of the filtered optical signal from a time domain to a frequency domain;
determine the magnitude of the estimated heart rate frequency based on the transformed filtered optical signal; and
determine magnitudes of heart rate frequencies within a threshold of the estimated heart rate frequency based on the transformed filtered optical signal.

13. The optical heart rate sensor of claim 12, wherein the recent window of the filtered optical signal is a recent five second window.

14. The optical heart rate sensor of claim 10, wherein an amount of motion signal filtering remains constant with changing motion frequency.

15. A method of optical heart rate sensing, comprising:
receiving a motion frequency via a motion sensor;
receiving an optical signal from an optical sensor;
filtering the motion frequency from the optical signal with an amount of filtering that is independent of the motion frequency;
determining an estimated heart rate frequency based on the filtered optical signal;
determining a probability that the estimated heart rate frequency is the current heart rate frequency, including
transforming a recent window of the filtered optical signal from a time domain to a frequency domain;
determining a magnitude of the estimated heart rate frequency based on the transformed filtered optical signal; and
determining magnitudes of heart rate frequencies within a threshold of the estimated heart rate frequency based on the transformed filtered optical signal; and
reporting a heart rate based on the estimated heart rate frequency responsive to the probability that the estimated heart rate frequency is the current heart rate frequency being greater than a confidence threshold.

16. The method of claim 15, wherein filtering the optical signal based on the motion frequency includes applying a comb filter to the optical signal.

17. The method of claim 16, wherein filtering the optical signal based on the motion frequency further includes:
adjusting one or more parameters of the comb filter based on a recent motion frequency while maintaining the amount of filtering.

18. The method of claim 15, further comprising:
determining a local neighbor magnitude ratio of the filtered optical signal comprising a ratio of the magnitude of the estimated heart rate frequency to a sum of the magnitudes of heart rate frequencies within a threshold of the estimated heart rate frequency; and
comparing the local neighbor magnitude ratio to the confidence threshold.

* * * * *